(12) United States Patent
Mayer et al.

(10) Patent No.: US 9,983,160 B2
(45) Date of Patent: May 29, 2018

(54) ELECTRODE ARRAY AND METHOD FOR OPERATING THE ELECTRODE ARRAY

(75) Inventors: Dirk Mayer, Frechen (DE); Yaqing Liu, Changchun (CN); Andreas Offenhaeusser, Eynatten (BE)

(73) Assignee: Forschungszentrum Juelich GmbH, Juelich (DE)

( * ) Notice: Subject to any disclaimer, the term of this patent is extended or adjusted under 35 U.S.C. 154(b) by 903 days.

(21) Appl. No.: 14/125,416

(22) PCT Filed: Jun. 12, 2012

(86) PCT No.: PCT/DE2012/000616
§ 371 (c)(1),
(2), (4) Date: Apr. 10, 2014

(87) PCT Pub. No.: WO2013/013649
PCT Pub. Date: Jan. 31, 2013

(65) Prior Publication Data
US 2014/0216947 A1    Aug. 7, 2014

(30) Foreign Application Priority Data

Jul. 28, 2011    (DE) .................. 10 2011 108 885

(51) Int. Cl.
*G01N 27/27* (2006.01)
*G01N 27/327* (2006.01)
(52) U.S. Cl.
CPC ......... *G01N 27/27* (2013.01); *G01N 27/3277* (2013.01)
(58) Field of Classification Search
CPC .................. G01N 27/27; G01N 27/3277
See application file for complete search history.

(56) References Cited

U.S. PATENT DOCUMENTS 6,262,264 B1 * 7/2001 Buck, Jr. ............. C07F 15/0026
205/792
2002/0110831 A1    8/2002 Schlag
(Continued)

FOREIGN PATENT DOCUMENTS

JP         62-11159      1/1987
JP         3-502149      5/1991
(Continued)

OTHER PUBLICATIONS

XP55040180 : Yaqing Liu et al., "An Electrochemically Transduced XOR Logic Gate at the Molecular Level", p. 1.
(Continued)

*Primary Examiner* — Gurpreet Kaur
(74) *Attorney, Agent, or Firm* — Norris McLaughlin & Marcus, P.A.

(57) ABSTRACT

An electrode array for the cyclic reduction and oxidation of a redox species in an electrolyte, wherein both electrodes are disposed on an insulating substrate and connected to a counter electrode for the application of a voltage, comprising: 1) a control electrode for reacting the redox species for cyclic electron transport between the electrodes: and b) a collector electrode disposed opposite the control electrode, wherein a layer structure composed of a second insulator and a charge transfer mediator disposed thereon is additionally disposed on the side of the collector electrode located opposite the insulating substrate for reacting the redox species. Two methods for operating the electrode array are disclosed.

10 Claims, 8 Drawing Sheets

(56) References Cited

U.S. PATENT DOCUMENTS

| | | |
|---|---|---|
| 2002/0123048 A1* | 9/2002 | Gau, Jr. .............. B01L 3/5088 435/6.11 |
| 2006/0160100 A1 | 7/2006 | Gao et al. |
| 2007/0054317 A1 | 3/2007 | Diebold et al. |
| 2009/0101955 A1 | 4/2009 | Park |

FOREIGN PATENT DOCUMENTS

| | | |
|---|---|---|
| JP | 8-327579 | 12/1996 |
| JP | 2004-514890 | 5/2004 |

OTHER PUBLICATIONS

E. Tran, et al. "Gating current flowing through molecules in metal-molecules-metal junctions", p. 1.

XP55040180 : Yaqing Liu et al., "An Electrochemically Transduced XOR Logic Gate at the Molecular Level".

XP008121851 : Tucker J H R et al., "Recent developments in the redox-switching binding of organic compounds".

Habermueller, K. et al., "Electron-transfer mechanisms in amperometric biosensors".

Liu, Yaqing et al., "Electrochemical current rectification at bio-functionalized electrodes".

Yaqing Liu et al: "An Electrochemically Transduced XOR Logic Gate at the Molecular Level", Angewandte Chemie (International ED. In English), Bd. 122, Nr. 14, Mar. 29, 2010 (Mar. 29, 2010), Seiten 2649-2652, XP55040180, ISSN: 0044-8249, DOI: 10.1002/ange.200906333 in der Anmeldung erwaehnt das ganze Dokument.

Tucker J H R et al: "Recent developments in the redox-switching binding of organic compounds", Chemical Society Reviews, Chemical Society, London, GB, Bd. 31, Nr. 3, Jan. 1, 2002 (Jan. 1, 2002), Seiten 147-156, XP008121851, ISSN: 0306-0012, DOI: 10.1039/a8042511 |Gefunden AM Mar. 18, 2002| Zusammenfassung.

Habermueller, K., Mosbach, M., Schuhmann, W.: Electron-transfer mechanisms in amperometric biosensors, In: Fresenius Journal of Analytical Chemistry, vol. 366, 2000, S. 560-568.

Liu, Yaqing: Offenhaeusser, Andreas; Mayer, Dirk: Electrochemical current rectification at bio-functionalized electrodes. In: Bioelectrochemistry, vol. 77, 2010, S. 89-93.—ISSN 1567-5394.

E. Tran, M. Duati, G.M. Whitesides, M.A. Rampi (2006). Gating current flowing through molecules in metal-molecules-metal junctions. Faraday Discuss., 2006, 131, 197-203).

Liu, Yaqing et al., An Electrochemically Transduced XOR Logic Gate at the Molecular Level, Angew. Chem. Int. Ed. 2010, vol. 49, p. 2595-2598.

* cited by examiner

ELECTRODE ARRAY AND METHOD FOR OPERATING THE ELECTRODE ARRAY

The invention relates to an electrode array and to a method for operating the electrode array.

BACKGROUND OF THE INVENTION

Existing transistors are based on semiconducting solid bodies or molecules.

The drawback of transistors according to the prior art is that switch effects are created by space charge layers that extend significantly. For chemical sensor functions, molecular or biological functions must be further added to the transistor at the semiconducting layers. The disadvantage is that this worsens electric coupling. This results in reduction in sensitivity, long reaction times, or even signal loss.

It is known from Liu et al. (Y. Liu, A. Offenhäusser, D. Mayer (2010). An Electrochemically Transduced XOR Logic Gate at the Molecular Level. Angew. Chem. Int. Ed., 49, 2595-2598) to provide an electrode array having a charge transfer mediator and a redox species. The array ensures charge transfer in a direction of the electrode array.

It is known from Tran et al. (E. Tran, M. Duati, G. M. Whitesides, M. A. Rampi (2006). Gating current flowing through molecules in metal-molecules-metal junctions. Faraday Discuss., 2006, 131, 197-203) to allow a current to flow between molecules of a metal-molecule-metal junction. The disadvantage is that it is not possible with this array to induce a reproducible current flow in the metal-molecule-metal junction.

It is the object of the invention to provide an electrode array that can be operated as an electric switch, while avoiding the disadvantages of semiconducting transistors from the prior art. In contrast to the existing electrode/electrolyte arrays, the electrode array is directed to achieving reproducible results with respect to information coding.

The object is achieved by an electrode array and by the method for operating the electrode array. Advantageous embodiments will be apparent.

SUMMARY OF THE INVENTION

The electrode array comprises a control electrode and a collector electrode. The array composed of the control electrode and the collector electrode is suited for cyclic reduction and oxidation of a redox species in an electrolyte. The control electrode and the collector electrode are disposed on an insulating substrate. The electrodes are additionally connected to a counter electrode for the application of a voltage to these. The electrode array thus comprises:

a) the control electrode for the initializing reaction of the redox species for cyclic electron transport between the control electrode and the collector electrode; and b) a collector electrode disposed opposite the control electrode, wherein a layer structure composed of a second insulator and a charge transfer mediator disposed thereon is additionally disposed on the side of the collector electrode located opposite the insulating substrate for reacting the redox species in the electrolyte.

The electrode array is suited for cyclic reduction and oxidation of a redox species in an electrolyte, and carries these out at the electrodes, in keeping with the voltages that are applied by the counter electrode. The control electrode and the collector electrode are immersed in the electrolyte for this purpose. The electrically active (molecule) layer of the charge transfer mediator comprises groups that can perform the charge transfer with the redox species in the environment, which is to say with molecules in (electrolyte) solution.

The control electrode and the collector electrode are disposed on an insulating substrate. Both electrodes are connected to a counter electrode for the application of a voltage, wherein the counter electrode can additionally have the function of a reference electrode. The circuit is implemented, for example, in an operational amplifier as a bipotentiostat (for example Metrohm Autolab Bipotentiostat PGSTAT 30) for adjusting the applied voltages.

It goes without saying that the indicated potentials at the control electrode and the collector electrode can be measured compared to a separate reference electrode.

The charge transfer mediator picks up the electrons of the redox species, provided that the standard electrode potential of the charge transfer mediator is more positive than the standard electrode potential of the redox species in the electrolyte. Conversely, the charge transfer mediator gives off electrons to the redox species, provided the standard electrode potential of the redox species is more positive than that of the charge transfer mediator.

The charge transfer mediator is surrounded by the additional insulator on the collector electrode between the same and the charge transfer mediator, and thus advantageously produces a rectifier function. The insulator suppresses direct charge transfer between the redox species and the collector electrode. A charge transfer from the collector electrode to the redox species, or vice versa, thus only takes place via the charge transfer mediator. At a predetermined potential at the collector electrode and at the control electrode, the interaction between the collector electrode as well as the second insulator disposed thereon and the charge transfer mediator not only allows the electrode array as a whole to be operated as an electrochemical switch for informational 0/1 binary encryption, but additionally causes the same to have an amplifier function.

It was recognized as part of the invention that the Hg-SAM-R-R-SAM-Hg junctions from the prior art are prone to problems, regardless of the toxic properties thereof. This is due to the softness of the material and the principle of reciprocal action due to the direct contact of the two dropping mercury electrodes. This prevents reproducible measurement results. In contrast, the electrode array according to the invention has well-defined and integratable contact surfaces at the electrodes. At a particular concentration of the reactants, due to the voltages applied to the collector electrode and to the control electrode, a more reproducible current flow is generated, as compared to the metal-molecule-metal junctions known from the prior art.

In one embodiment of the invention, the control electrode and the collector electrode are made of the same material. This advantageously allows the electrodes to be produced in almost an identical manner, or even in the same process.

In a further embodiment of the invention, the electrode array comprises a control electrode and a collector electrode, which have a constant distance of less than 10 μm from each other. This ensures that the redox species can easily migrate from one electrode to the other for the purpose of renewed reaction, such as by way of diffusion.

The control electrode and the collector electrode can, in particular, be disposed so as to mutually engage each other in an interdigitating structure having a meandering shape, with respect to each other. This advantageously allows a rapid transfer of a large number of molecules of reduced or oxidized redox species between the control electrode and the collector electrode, whereby the above-mentioned process for the implementation of electrical circuits is maintained by the cyclic reaction of the redox species and electron transport.

The method for producing the electrode array can be carried out as follows, for example. An insulating layer, for example a silicon oxide, is disposed on a (semiconductor) substrate. A silicon wafer can preferably be oxidized for this purpose. If the substrate itself is already insulating, this step is not required. The electrodes are preferably produced by way of lithography, for example using a lift-off process of an applied photoresist, since these processes are standardized. The electrodes can have a thickness of 200 nm and preferably be made of metal, in particular vapor-deposited gold. An adhesion promoter, for example made of chromium or titanium, can be applied to the substrate/insulator array and structured together with the gold for better adhesion between the substrate/insulator array and the (gold) electrode. The electrodes are preferably dipped into an ethanolic mixture of insulating molecules and redox mediator molecules, applied to the electrodes in a self-organizing manner. By way of example, a mixture made of insulating 1-hexadecanethiol (HDT) and electroactive redox mediator molecules, such as 11-undecanethiol ferrocene (Fc) in ethanol, which are covalently bound to the collector electrode, shall be mentioned. The concentration of hexadecanethiol is 1 mM, for example, and the concentration of 11-undecanethiol ferrocene is likewise 1 mM in ethanol, for example. The immersion time is generally 24 hours, but is not less than 10 minutes. Thereafter, the mixture is rinsed at least once in pure ethanol. Advantageously, monolayers of the molecules are applied to the electrodes in a self-organizing manner. Up to this step, the two electrodes are advantageously produced in an identical manner. Thereafter, the layer made of the second insulator, including the charge transfer mediator, is once again removed from the control electrode by way of electrodesorption. The desorption is carried out in a low-proton electrolyte, for example in a 10 mM aqueous solution of sodium hydroxide. A negative desorption voltage, for example of −1 V (SCE), is applied to the control electrode for at least 20 seconds. The collector electrode remains non-polarized. Thereafter, a rinsing step is carried out with deionized water.

In addition to arranging the collector electrode and the control electrode in the same plane on the substrate insulator, the control electrode and the collector electrode can also be located in levels on top of each other, for example in a channel. Such electrodes can be produced by way of etchable sacrificial layers, such as chromium, between the electrodes. The control and collector electrodes can also be produced separately from each other and positioned on top of each other. The distance between the electrodes is adjusted for this purpose using micropositioners.

Particularly advantageously, the method for operating an electrode array provides for a charge transfer mediator and a redox species in the electrolyte being selected having a respective standard electrode potential which, depending on the voltages that are applied between the counter electrode and the control electrode, and between the counter electrode and the collector electrode, allows a charge transfer along the electrochemical series, which is to say in the direction of a respective more positive $E_0$ between the redox partners, and keeps it going. The reaction of the redox species at the two electrodes takes place cyclically and can be detected by measuring the resulting current. This means that, following oxidation at one of the two electrodes, the redox species is reduced at the other electrode. The cycle of reaction then begins again (cyclic reaction).

The redox partners involved, which is to say the redox species and the charge transfer mediator, are thus reduced and oxidized at the control electrode and the collector electrode by the application of suitable voltages.

Two different methods of circuiting the electrode array are possible for this purpose. In a first embodiment of the method of circuiting the electrode array, an electron transfer from the control electrode to the oxidized redox species that is added to the electrolyte is induced as an initiating, activating step by the voltages that are applied to the collector electrode and to the control electrode. Thereafter, the redox species thus reduced is transported to the collector electrode, where it is oxidized again. The electron transfer takes place from the redox species via the charge transfer mediator to the collector electrode for this purpose. In the second embodiment of circuiting, an electron transfer is induced as an initiating, activating step by the applied voltages from the reduced redox species to the control electrode. The oxidized form diffuses to the collector electrode. From the collector electrode, the electron transfer then takes place via the charge transfer mediator to the oxidized redox species.

In the first embodiment of the method, a redox species having a more negative standard electrode potential than that of the charge transfer mediator is added in oxidized form to the electrolyte for this purpose. For example, the redox species hexocyanoferrate having the redox couple hexacyanoferrate(II)/hexacyanoferrate(III), hereinafter referred to as Ferro II/Ferri III, can be selected. The standard electrode potential thereof is approximately 0.2 V (SCE). The charge transfer mediator selected in this case can be 11-undecanethiol ferrocene (Fc) having a standard electrode potential of approximately 0.34 V (SCE), for example.

In the second embodiment of the method, a redox species having a more positive standard electrode potential than that of the charge transfer mediator, for example an iridate having the redox couple iridium hexachloride(III)/iridium hexachloride(IV), hereinafter referred to as Iridate III/Iridate IV, can be selected as the redox species and added in reduced form to the electrolyte. The standard electrode potential of this redox species is approximately 0.71 V (SCE). The use of Iridate III/IV results in an alternative circuiting method as compared to that using hexacyanoferrate, if a charge transfer mediator having a more negative standard electrode potential than that of Iridate III/IV is selected, such as 11-undecanethiol ferrocene (Fc) (0.34 V, SCE).

The redox species is thus added in oxidized form to the electrolyte in the first method, for example as Ferri III, and is added in reduced form in the second method, for example as Iridate III.

In the first embodiment of the method, voltages are applied between the counter electrode and the control electrode, and between the counter electrode and the collector electrode, by the voltage sources, using the operational amplifier, so that a potential more negative than the standard electrode potential of the redox species is present at the control electrode, and a potential more positive than the standard electrode potential of the charge transfer mediator is constantly present at the collector electrode. This advantageously causes the oxidized form of the redox species to be initially activated at the control electrode as a result of reduction. The further charge transfer then takes place after diffusion of the redox species in the electrolyte to the collector electrode. The charge transfer takes place between the reduced form of the redox species to the charge transfer mediator, and from there to the collector electrode. The collector electrode has the most positive potential of all the redox partners that are involved. As a result of the oxidation of the redox species at the charge transfer mediator, the starting product, which is to say the redox species in oxidized form, is again provided. The cyclic reaction of the redox species begins again following the diffusion at the control electrode.

In the second embodiment of the circuiting method, a redox species having a more positive standard electrode potential than the standard electrode potential of the charge transfer medium is added to the electrolyte, for example an iridium hexachloride having the redox pair Iridate III/Iridate IV. The redox species is added in reduced form to the electrolyte, for example as Iridate III. A potential that is more negative than the standard electrode potential of the charge transfer mediator is constantly applied to the collector electrode, and a potential that is more positive than the standard electrode potential of the redox species iridate is applied to the control electrode. This advantageously causes the reduced form of the redox species to be initially activated at the control electrode due to oxidation. In addition, the fact that the potential at the collector electrode is more negative than the standard electrode potential of the charge transfer mediator advantageously causes electrons to be transferred starting from the collector electrode via the insulator to the charge transfer mediator. This reduces the charge transfer mediator. Since the standard electrode potential of the redox species is more positive than the standard electrode potential of the charge transfer mediator, diffusion of the redox species to the collector electrode is followed by the reduction of the redox species at the charge transfer mediator which, in the case of Iridate IV, is into Iridate III. The charge transfer mediator is oxidized. The reduced redox species, for example Iridate III, again diffuses to the control electrode having the most positive potential, where it is again oxidized. The cycle thus begins again.

The insulator disposed on the collector electrode between the electrode and the charge transfer mediator prevents direct charge transfer between the redox species and the collector electrode.

By modulation of the voltage at the control electrode, the electrode array can be operated as an electrochemical switch and transistor, which can be used to switch a current flow on and off, and to amplify the same, as a function of the voltages that are present at the collector electrode and the control electrode. By following the potential window at the control electrode, the electrode array will, of course, implement the amplifier function. The electrode array can thus be operated as an electrochemical transistor.

For this purpose, the potential at the collector electrode is constantly adjusted to be more positive than the standard electrode potential of the redox species in the first embodiment of the circuiting method. Starting from a more positive value, the voltage U at the control electrode is modulated toward a cathodic, which is to say more negative, potential than the standard electrode potential of the redox species. As soon as the voltage at the control electrode approximately reaches the standard electrode potential of the redox species, and is shifted beyond that in the direction of a cathodic, which is to say more negative, potential, the current at the collector electrode is amplified. The amplification current can be converted into an amplification voltage, for example by way of a defined resistance.

In the second exemplary embodiment, the voltage at the collector electrode is constantly adjusted to be more negative than the standard electrode potential of the charge transformer mediator and of the redox species. Thereafter, the voltage U is successively modulated at the control electrode from an initially more negative value than the standard electrode potential of the redox species in the direction of the standard electrode potential of the redox species. As soon as the voltage at the control electrode reaches the standard electrode potential of the redox species, and is shifted beyond that in the direction of an anodic, which is to say more positive, potential, the signal is amplified.

Low modulations of the voltages of the control electrode achieve a high amplification effect.

In both embodiments, the charge transfer takes place along the electrochemical series in the direction of a respectively more positive standard electrode potential ($E_0$) of the involved redox partners. The charge transfer always takes place when the charge carrier continually reaches states of lower energy, from the source to the end point. The individual states are separated from each other by barriers which must be overcome by tunneling processes or by field emission.

In the first method of circuiting the electrode array, it is not possible to add a reduced form, and in the second method it is not possible to add an oxidized form, of a redox species to the electrolyte. During the first embodiment, for example using Ferro II instead of Ferri III, the electron transport starting with the charge transfer would be induced by the presence of the reduced form of the redox species, without influence by the control electrode, directly at the collector electrode. The subsequent cyclic activation of comparatively few molecules of the redox species at the control electrode as compared to the concentration of the molecule would only result in a very small difference in the subsequently measured voltage at the collector electrode, so that a switch operation or a detection reaction would no longer be reliably detectable. In the second alternative method, the charge transfer would take place directly, without any influence by the control electrode, from the collector electrode via the charge transfer mediator to the redox species.

All the settings of the voltages at the control electrode and at the collector electrode take place via the counter electrode, for example a platinum wire.

In both of the described methods for circuiting the electrode array, an upper and a lower limit current are established for the function as an electrochemical switch, and when these limits currents are exceeded or no longer met, the charge transfer at the collector electrode is established as a bit with a positive event (one) or negative event (zero). This is necessary for switch functions for coding the information. The invention is thus suited for carrying out electrical switch functions. For this purpose, the voltage of the collector electrode is set to a fixed value, and the current is measured as a signal. By modulation of the voltages at the control electrode to values above and below the standard electrode potential of the redox species, the charge transfer and current at the collector electrode can be selectively amplified in a the manner of a transistor. The current can thus be switched off and on so as to encode information. The function is dependent on the redox species in the environment of the electrodes, the nature of the charge transfer mediator at the collector electrode, the concentration of the redox species, and the voltages present at the collector electrode and at the control electrode.

The circuiting of the electrode array and the detection of instances where the limit currents at the electrodes are not met or exceeded are advantageously carried out in a computer-assisted manner and are stored.

All charge transport processes take place by way of the discrete redox states of the redox partners. The switching function is carried out by way of a layer of the charge transfer mediator which measures a few nanometers thick and is disposed on the insulator. The charge transfer mediator is in contact with the redox species in the electrolyte. The electrodes, the charge transfer mediator and the redox species are separated from each other by energy barriers. The collector electrode has a rectifier function with the insulator and the charge transfer mediator, and the control electrode has a control function for the provision of the redox species. The transport distance of the charges, or the extent of the barrier, is generally less than 10 nm. The charge transport thus essentially takes place by way of tunneling processes and field emission.

If the electrode array is to represent a sensor, charge transfer is preferably possible only between a particular redox species and a particular charge transfer mediator, for example based on detection reactions according to the key-lock principle or the steric circumstances of the involved molecules. For this purpose, in particular enzymes and the substrates thereof may be used. The invention is then used to identify and detect a specific redox species in solution. The sensory system and the signal conversion system then form one unit. For this purpose as well, a molecular layer is coupled to the collector electrode, which is composed of insulating and electrically active charge transfer mediators.

The electrically active charge transfer mediator molecules can also be replaced by redox-active inorganic compounds.

The invention will be described in more detail hereafter based on exemplary embodiments of the electrode array (FIGS. 1 to 3 and Table 1) and two methods of circuiting based on the accompanying drawings, without thereby limiting the invention.

DETAILED DESCRIPTION OF THE PREFERRED EMBODIMENTS

All the listed potentials at the electrodes were measured with respect to a separate reference electrode (SCE). The potentials are indicated relative to a saturated calomel electrode (SCE).

Figure 1:
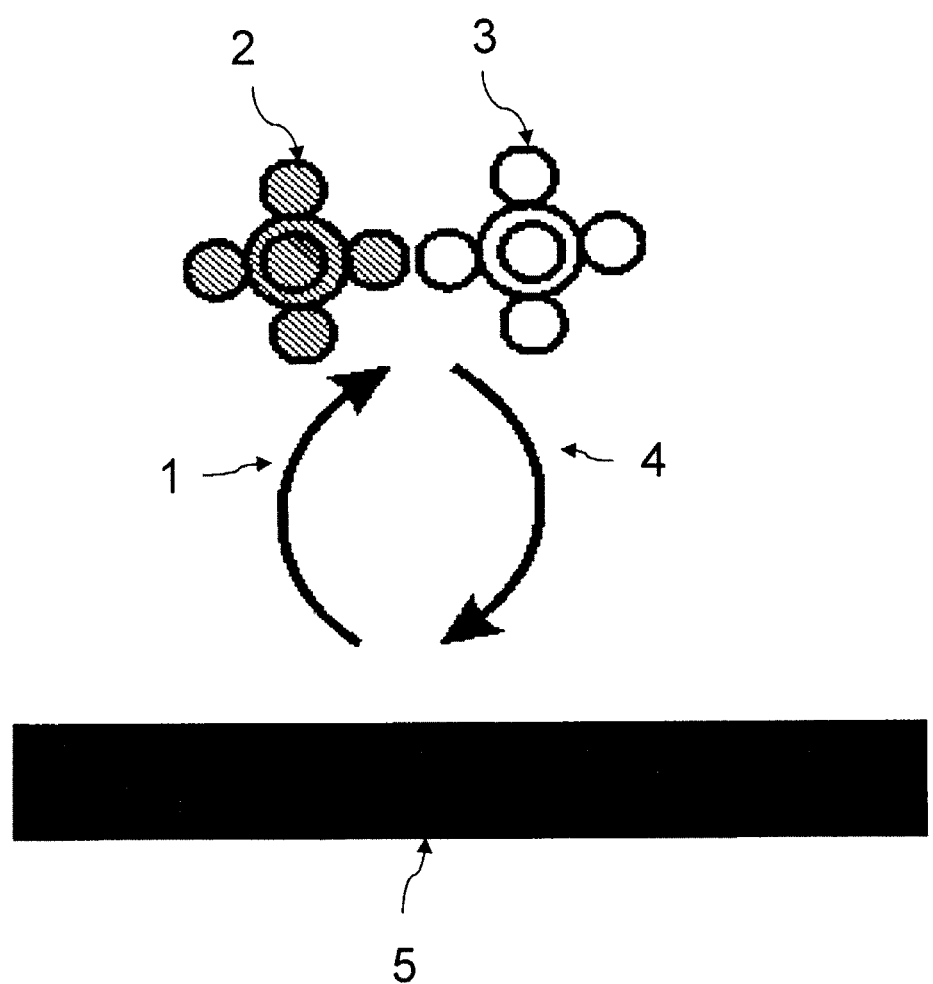
FIG. 1: shows the control electrode.

FIG. 1 shows a possible sub-process at the control electrode 5 according to the first embodiment of the method of circuiting. The control electrode is made of gold, which is disposed on an insulating substrate (not shown). The gold electrode 5 is produced by way of lithography using a lift-off process of a photoresist according to standard processes. In contrast to the collector electrode, the control electrode 5 does not include any further molecule layers thereon comprising the insulator and the charge transfer mediator. The control electrode directly activates the redox species 2, which is added in oxidized form, which here is Ferri III, and more particularly by way of reduction step 1. For this purpose, a potential that is more negative than the standard electrode potential of the redox species hexacyanoferrate is applied to the control electrode via a counter electrode, which is not shown. As a result of the charge transfer from the control electrode 5 to Ferri III, this is reduced to Ferro II 3.

In theory, Ferro II 3 can be deactivated again at the control electrode 5 in FIG. 1 using an oxidation step 4. This would result in a charge transfer from Ferro II to the control electrode 5 and Ferri III would be created again. In the first circuiting method of the electrode array, this is prevented by the application of a voltage from the counter electrode (not shown) to the control electrode 5 which is more negative than the standard electrode potential of the redox species hexocyanoferrate, so that Ferro II 3 can only diffuse to the collector electrode and can be oxidized there into Ferri III by way of the charge transfer mediator, see FIG. 2.

The collector electrode 25 is likewise made of gold for this purpose. The collector electrode 25 is provided with a self-organized monolayer of a mixture made of insulating molecules 24, here hexanedecanethiol (HDT) and electroactive redox mediator molecules 21, here 11-undecanethiol ferrocene (Fc), for example. The charge transfer mediator has a standard electrode potential of approximately 0.34 V. The ferrocene group can be reduced and oxidized, while the undecanethiol and the hexanedecanethiol are disposed in a self-organizing manner on the electrode.

The redox species used can be the redox couple Ferro II/Ferri III (standard electrode potential: 0.23 V), or in the alternative method also Iridate (standard electrode potential: 0.71 V). The redox couple Ferro II/Ferri III has a more negative standard electrode potential than 11-undecanethiol ferrocene (Fc). The redox couple Iridate III/Iridate IV has a more positive standard electrode potential than 11-undecanethiol ferrocene (Fc). Accordingly, according to the two embodiments of circuiting, the voltage must be adapted to the control electrode and the collector electrode via the counter electrode for a cyclic charge transfer, and the diffusion of the redox species between the electrodes must be ensured. The functions as an electrochemical switch and as a transistor are implemented as follows:

First Embodiment of Circuiting: The Standard Electrode Potential of the Redox Species is More Negative than the Standard Electrode Potential of the Charge Transfer Mediator (FIG. 2)

The oxidized Ferri III is added to the electrolyte, here PBS (pH 5.6). A voltage that is lower than the standard electrode potential of hexocyanoferrate is applied to the control electrode via the counter electrode. Ferri III is reduced to Ferro II at the control electrode, see FIG. 1. Ferro II diffuses to the collector electrode 25. As with the control electrode, the collector electrode is disposed on the insulating substrate (not shown).

Ferro II 23 is oxidized at the collector electrode to Ferri III 22 by way of the charge transfer mediator 11-undecanethiol ferrocene (Fc) 21 since the potential of the charge transfer mediator is more positive than the standard electrode potential of the redox species (electrochemical series). Ferri III 22 itself cannot exchange any further charges with the mediator 21 since the charge transfer always takes place only when the charge carrier continually reaches states of lower energy from the source to the end point. This is illustrated in FIG. 2 by the crossed-out arrow. The charge transfer then further takes place from the charge transfer mediator 21 via the insulator 24 to the gold electrode 25, since a potential that is more positive than that of the redox species and of the charge transfer mediator is applied thereto via the counter electrode (not shown). Following the oxidation into Ferri III 22, this again diffuses to the control electrode, and the process starts again.

Figure 2:
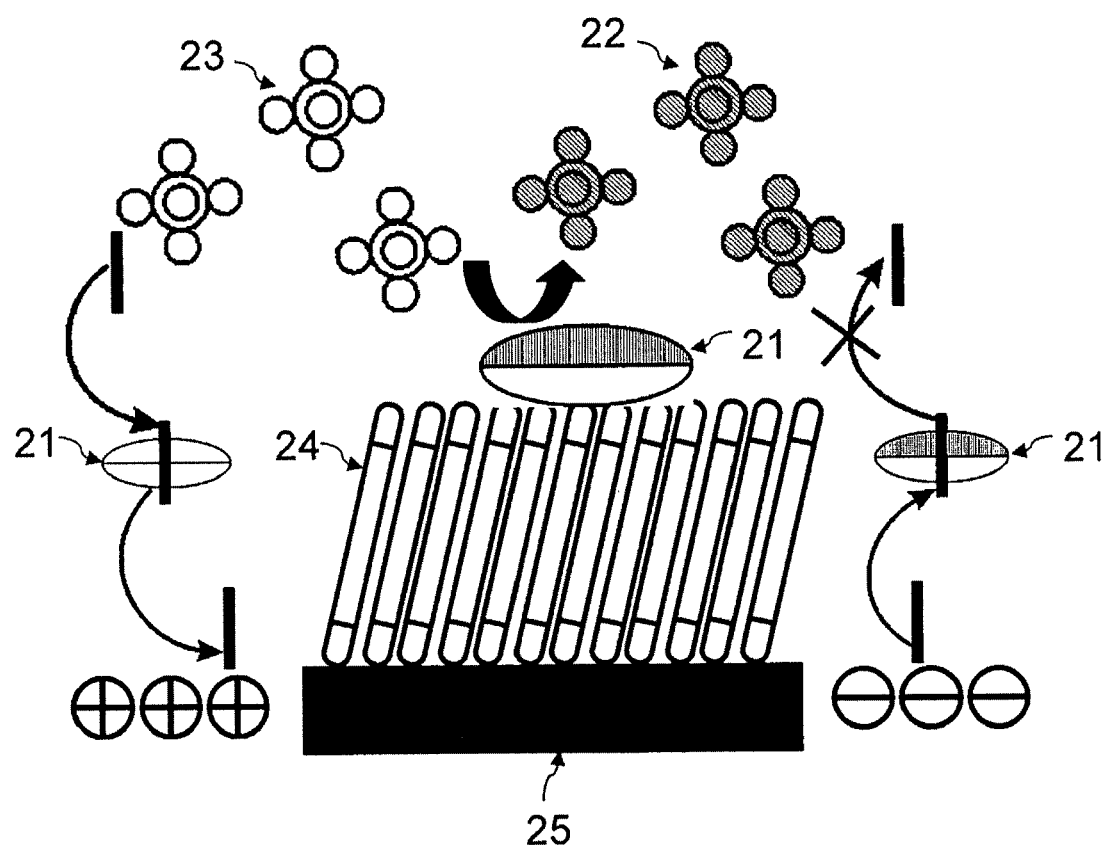
FIG. 2: shows the collector electrode.

The energy barriers are indicated by vertical thick bars in FIG. 2 and show that a charge transfer from the collector electrode 25 to the charge transfer mediator is not possible at the indicated standard electrode potentials of the redox partners hexocyanoferrate and 11-undecanethiol (Fc), and with the voltage that is applied to the collector electrode 25 being more positive than the charge transfer mediator.

Second Embodiment of Circuiting: The Standard Electrode Potential of the Redox Species is More Positive than the Standard Electrode Potential of the Charge Transfer Mediator The flow of the charge transfer takes place according to the same mechanisms, entirely opposite to that of FIGS. 1 and 2. In the second embodiment, the reduced form Iridate III is added to the electrolyte, here 0.1 M perchloric acid. The redox pair Iridate III/Iridate IV has a standard electrode potential of approximately 0.7 V, which is more positive than the standard electrode potential of the charge transfer mediator 11-undecanethiol ferrocene (Fc) (0.34 V). A charge transfer that takes place opposite to that of FIGS. 1 and 2 can then be achieved as follows. Iridate III diffuses to the control electrode. A voltage is applied thereto via the counter electrode which is more positive than the standard electrode potential of Iridate III/Iridate IV, for example 0.8 V. The charge transfer thus takes place from Iridate III to the control electrode. As a result, Iridate IV is formed. This cannot pick up any charges from the control electrode due to the voltage that is applied thereto. Iridate IV rather diffuses to the collector electrode. Via the counter electrode, which is connected to the bipotentiostat in the operational amplifier, a voltage that is constantly less than 0.34 V, which is the standard electrode potential of the charge transfer mediator, is applied to the collector electrode. The charge transfer then takes place from the collector electrode via the insulator to the charge transfer mediator 11-undecanethiol ferrocene (Fc) by way of a tunneling process. This mediator is reduced. The oxidized form Iridate IV is reduced to Iridate III by way of the charge transfer mediator at the surface of the collector electrode, whereby the charge transfer mediator 11-undecanethiol ferrocene (Fc) is oxidized. A charge transfer from Iridate III back to the collector electrode is not possible for thermodynamic reasons and due to the voltage that is present at the collector electrode. Iridate III rather diffuses to the control electrode, where the process of the cyclic charge transport begins again due to the voltage at the control electrode.

The concentrations of Ferri III and Iridate III in both methods are approximately 1 mM, respectively, in the electrolyte. The current flow can be interrupted or set in motion by way of the voltage that is constantly applied to the collector electrode and by modulating the voltage at the control electrode. For the first circuiting method, measurable voltage does not occur until the potential at the control electrode is more negative than the standard electrode potential of the redox species. For the second circuiting method, measurable voltage does not occur until the potential at the control electrode is more positive than the standard electrode potential of the redox species.

Figure 3A:
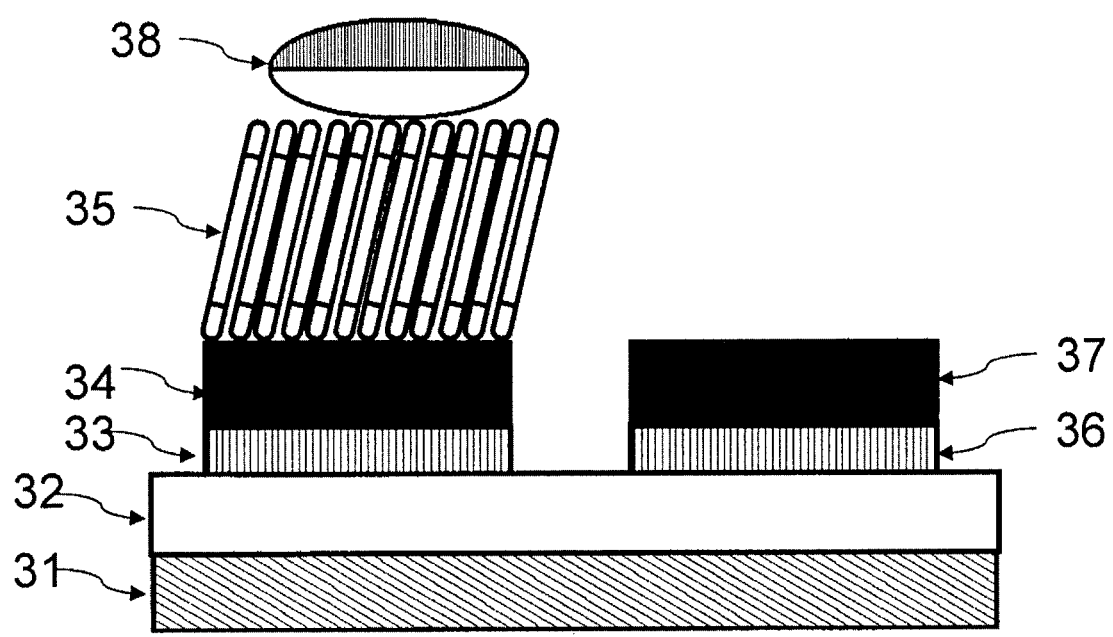
FIG. 3: shows the electrode design in a cross-sectional view (a) and as a block diagram (b)
Figure 3B:
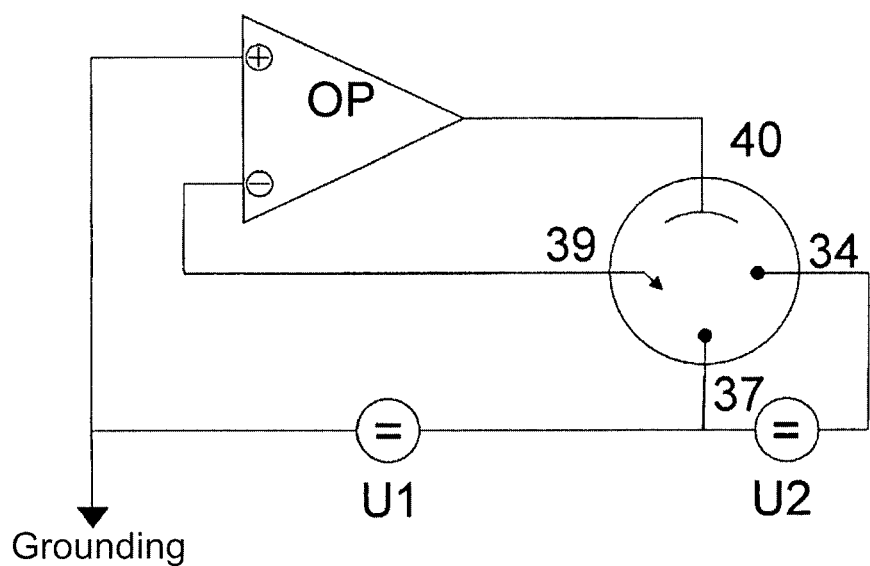

FIG. 3a is a schematic illustration of a side view of the control electrodes 36, 37 and of the collector electrodes 33, 34, 45. Both electrodes are disposed on a substrate made of a silicon wafer having a <110> orientation 31 and a $SiO_2$ layer 32. The $SiO_2$ layer is 400 nm thick and was grown on by way of wet oxidation. Both electrodes are produced by way of lithography, here by way of a lift-off process of a photoresist according to a standard process. Each of the gold electrodes 34, 37 has a thickness of 200 nm. A respective adhesion promoter 33, 36, which is made of 10 nm chromium or titanium and structured together with the gold, is applied between the substrates 31, 32 and the electrodes for better adhesion. A layer structure comprising the insulator hexanedecanethiol (HDT) 35 and electroactive redox mediator molecules 11-undecanethiol ferrocene (Fc) 38 is disposed on both gold electrodes. A monolayer of the molecules is simultaneously applied to the electrodes by way of a self-organization method from an ethanolic solution and is subsequently removed again from the control electrode 37 by way of electrodeposition. Both electrodes are connected to the counter electrode 40. FIG. 3b shows the circuit diagram of the electrode array. The operational amplifier comprises a computer. Reference numeral 39 denotes the reference electrode Ag/AgCl$_2$, reference numeral 40 denotes the counter electrode, and reference numerals 34 and 37 are the collector electrode and the control electrode, respectively. One end of the wire of the counter electrode is connected to a bipotentiostat having four electrical inputs (for example Metrohm Autolab Bipotentiostat PGSTAT 30), which fulfills the function of an operational amplifier. The other end is immersed into the electrolyte. Additionally, the reference electrode (for example SCE) is connected to the bipotentiostat. In the image of the operational amplifier, this corresponds to the negative input of the operational amplifier, which is preferably grounded. The control and collector electrodes are connected to the two remaining inputs of the bipotentiostat. In the image of the operational amplifier, this corresponds to the positive input of the operational amplifier. The bipotentiostat has two voltage sources, by way of which the voltages between the counter electrode and the collector electrode, and between the counter electrode and the control electrode, can be adjusted. The voltage sources are connected between the positive input of the operational amplifier and the control and collector electrodes. When the voltage between the counter electrode and the control electrode, or between the counter electrode and the collector electrode, is varied, a current is generated at the control electrode, or at the collector electrode, which corresponds to the ratio between the voltage and the associated impedance between the counter electrode and the control electrode or the collector electrode. The current at the collector electrode or at the control electrode, which results from a variation in the voltages, can be tracked separately by way of current measuring devices (for example, directly integrated into the Metrohm Autolab Bipotentiostat PGSTAT 30).

Figure 4:
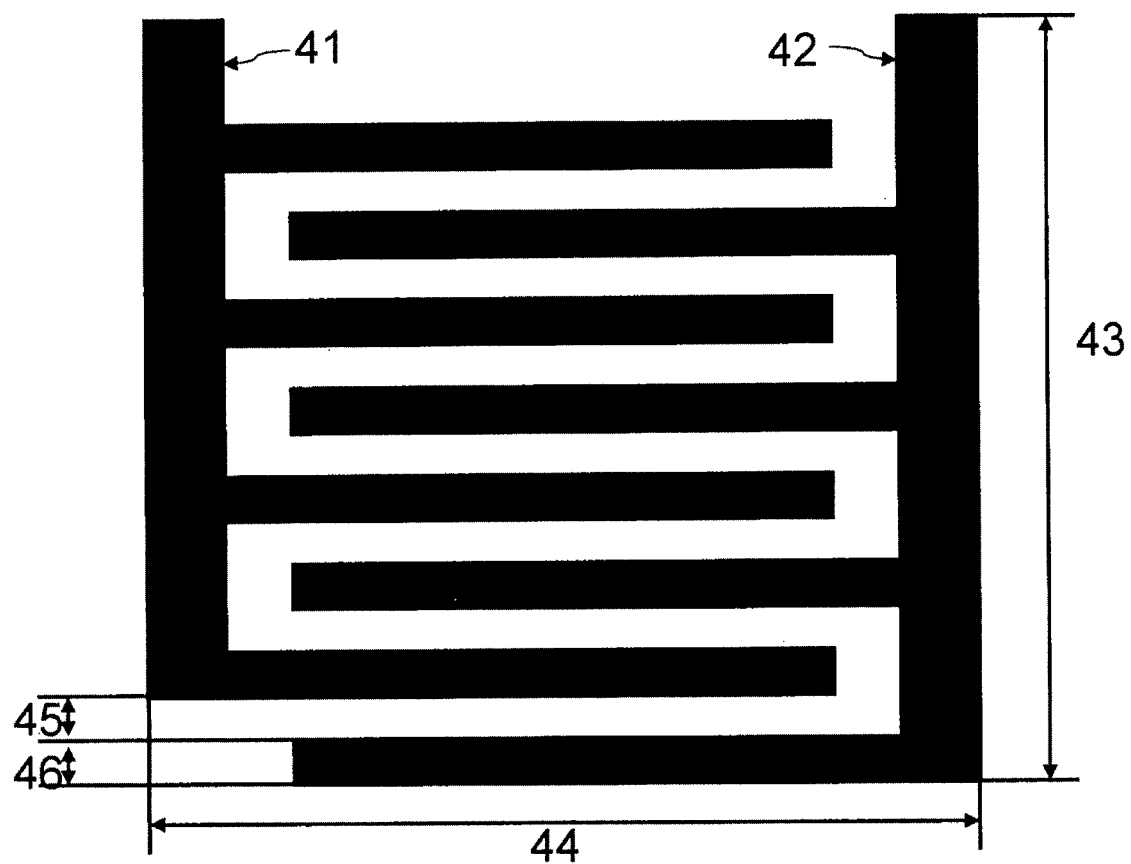
FIG. 4: shows an interdigitating electrode field.

An interdigitating electrode field comprising a collector electrode 41 and a control electrode 42 is shown schematically in a top view in FIG. 4. The redox species (not shown) can diffuse back and forth between the two electrodes. The control and collector electrodes are disposed opposite each other at a distance 45 of typically less than 10 μm, and in the present example approximately 2 μm. The distance 45 directly correlates with the response time of the switching processes, in that short distances result in short response times, and thus in short switching times. The electrodes have a width 46 that is approximately as large as the distance 45 (2 µm). However, the width of the electrodes may also be larger by up to a factor of 10 or more without impairing the operating principle of the invention. The width 46 of the electrodes should not be smaller than the distance of the electrodes from each other because otherwise the response times increase. The electrodes generally have considerably larger lengths 43 and 44 than widths 46. In this example, the electrodes are disposed opposite each other in a meander-shaped manner. This increases the electrode surface and thus improves the sensitivity.

Figure 5:
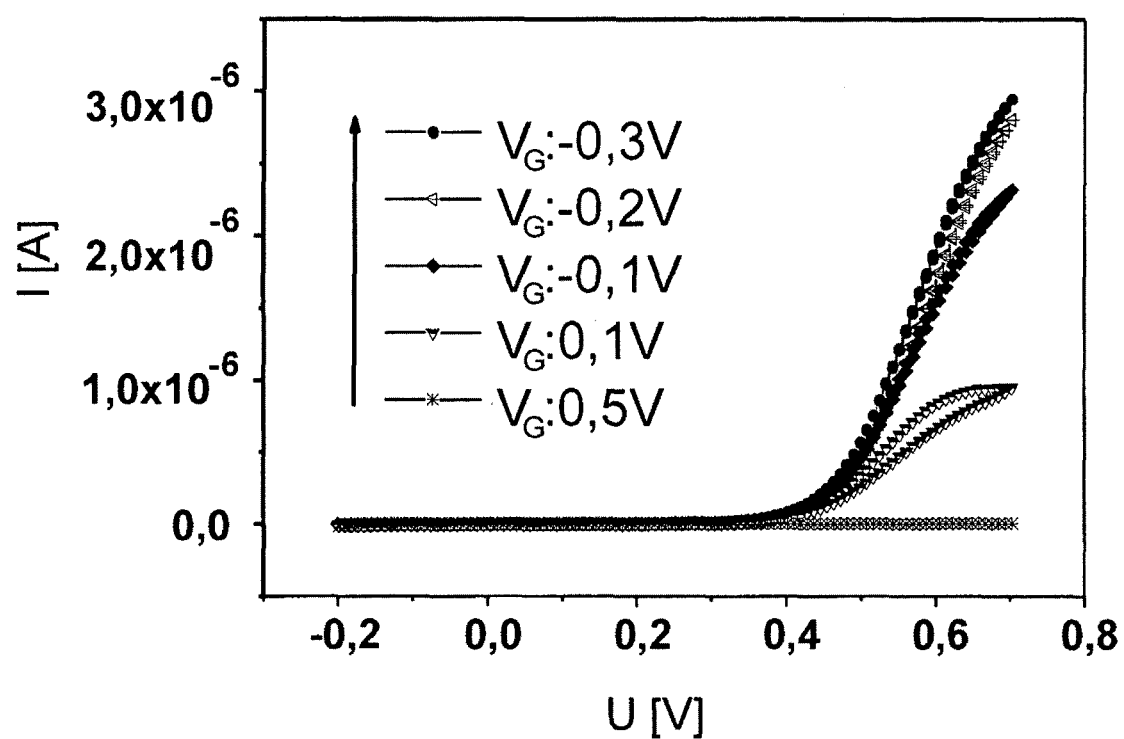
FIG. 5: shows an amplification effect: the dependency of the voltage as a function of the current at the collector electrode while modulating the voltage at the control electrode in method 1.

FIG. 5 shows the current I at the collector electrode as a function of the potential U at the collector electrode in phosphate buffer (PBS, pH 5.6) for the first circuiting method. If the voltage at the control electrode ($V_G$) is modulated and shifted past the standard electrode potential of Ferri III/Ferro II toward more cathodic (more negative) potentials, the anodic limit current of the collector electrode increases, since increasingly activated Ferro II is available. For this purpose, a more positive voltage than the standard electrode potential of the charge transfer mediator is applied to the collector electrode. The electrochemical switch exhibits transistor behavior.

Figure 6:
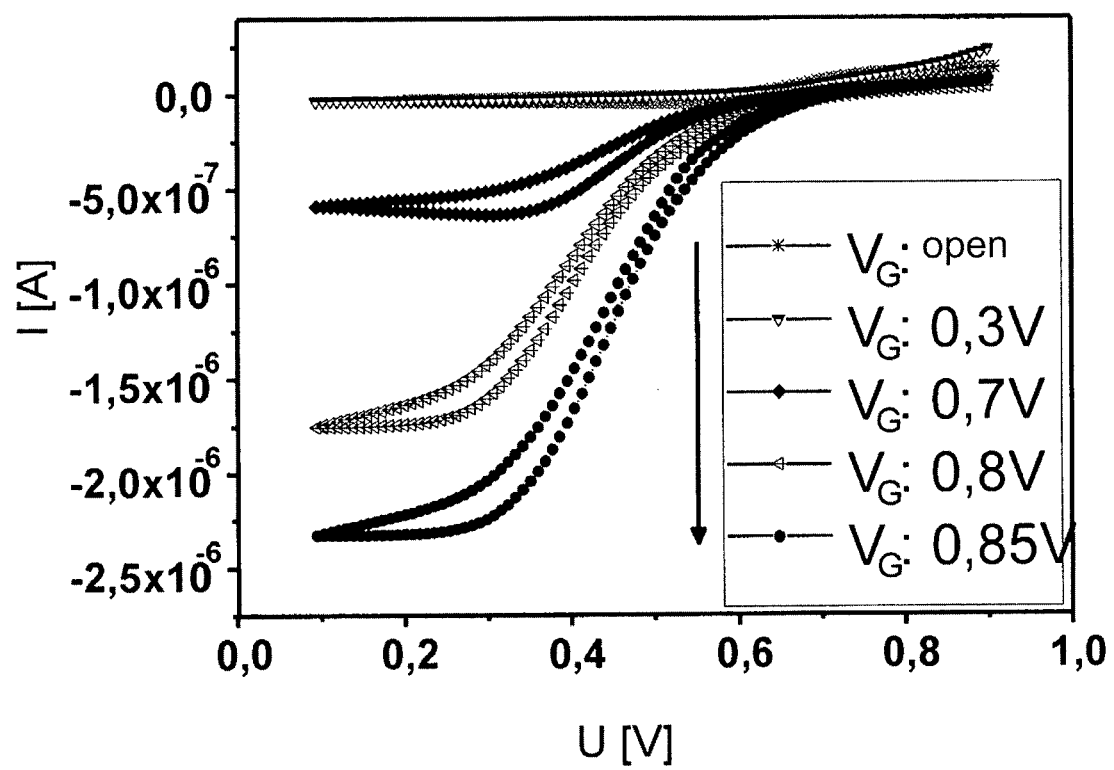
FIG. 6: shows an amplification effect: the dependency of the voltage as a function of the current at the collector electrode while modulating the voltage at the control electrode in method 2 (inverted)

FIG. 6 shows the current I at the collector electrode as a function of the potential U at the collector electrode in 0.1 M perchloric acid for the second circuiting method. If the voltage at the control electrode ($V_G$) is modulated, which is to say shifted past the standard electrode potential of Iridate III/Iridate IV toward more anodic (more positive) potentials, the limit current of the collector electrode increases, since increasingly more activated Iridate IV is available. The inversion of the characteristic curve as compared to FIG. 5 thus results from the replacement of the redox couple Ferri III/Ferro II with Iridate III/Iridate IV.

Figure 7:
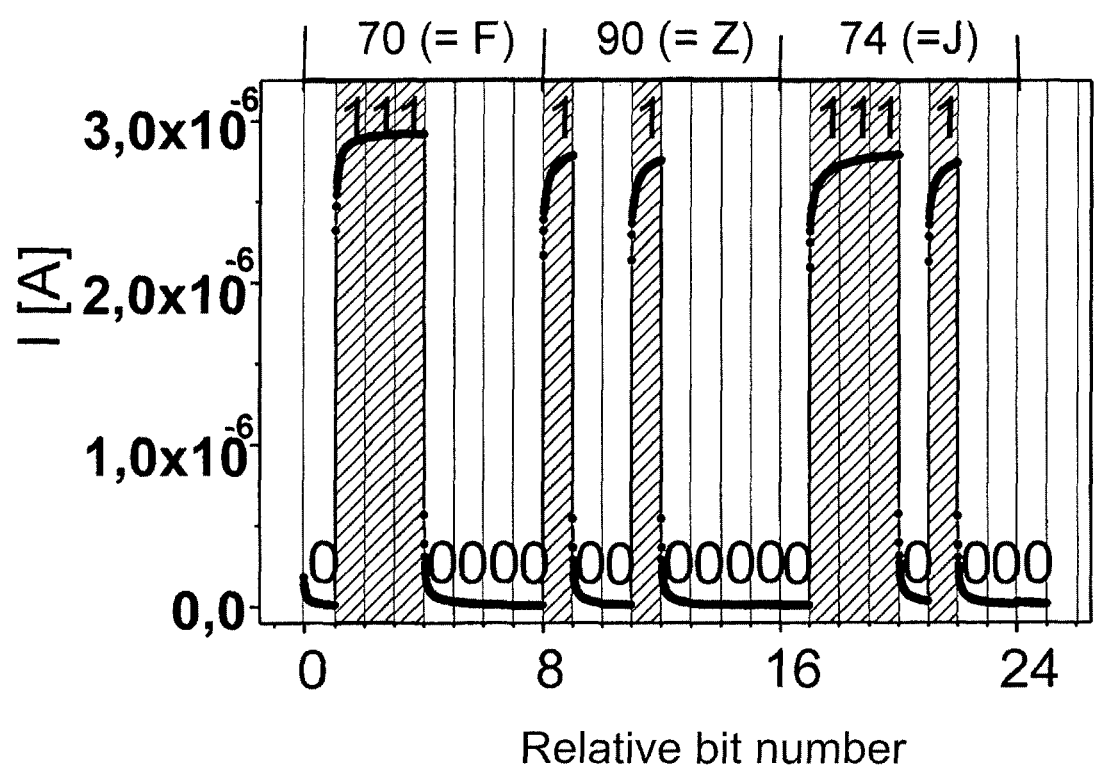
FIG. 7: shows a switch function for information encryption.

FIG. 7 shows the chronoamperometric switching function of the electrochemical transistor. The figure shows a 24-bit binary code for the encryption of in PBS (phosphate-buffered saline solution) (pH 5.6). Each letter corresponds to 8 bits. Current greater than 2.5 µA is accepted as 1, and current lower than 0.25 µA denotes 0. The binary code was additionally transferred into the hexadecimal code for encryption of the numbers 70 for F, 90 for Z, and 74 for J resulting from the binary code.

The potential of the control electrode influences how many Ferri III molecules must be activated into Ferro II at the control electrode. If the potential of the control electrode is more anodic (more positive) than the standard electrode potential of Ferri III, no Ferri III is activated into Ferro II. When the standard electrode potential of Ferri III at the control electrode has been reached, the amount of activated Ferro II increases drastically and goes into saturation. As a result, the anodic collector limit current increases when the control electrode drops below the standard electrode potential of Ferro II/Ferri III, see FIG. 5. Switching on and off the activation of Ferri III into Ferro II at the control electrode 5 by way of the electrode potential thereof thus controls the current at the collector electrode, see FIG. 5. The switching function is used for the binary coding of information. If the control electrode 5 switches to an electrode potential that is more anodic (more positive) than the standard electrode potential of the redox couple Ferri III/Ferro II, no collector current is measured. This corresponds to "current off", which is to say binary code 0, see FIG. 7. If the control electrode switches to an electrode potential that is more cathodic (more negative) than the standard electrode potential of the redox couple Ferri III/Ferro II, a collector current is measured. This corresponds to "current on", which is to say binary code 1. Conversely, electrons cannot be forwarded from Ferro II to the collector electrode by a potential of the collector electrode that is more cathodic (more negative) than the standard electrode potential of the transfer mediator, and the current drops to a limit current of 0, which is dominated by noise and parasitic components. In contrast, if Ferro II 23 is deactivated to Ferri III 22 at the collector electrode 25, these molecules can again diffuse to the control electrode, where they are reactivated into Ferro II.

In this way, information can be coded, see FIG. 7. The collector current here decisively depends on the concentration of the redox species in the solution.

The working direction according to the alternative circuiting method of this electrochemical transistor can be easily reversed by adding a reducing agent instead of an oxidizing agent as the redox species. The standard electrode potential thereof must be more anodic (more positive) than the standard electrode potential of the mediator, FIG. 6. The direction of the charge transfer here is opposite that of FIG. 5.

Further Exemplary Embodiments

It goes without saying that the selection of the redox species and of the charge transfer mediator, and the standard electrode potentials resulting therefrom, as well as the applied voltages, are provided only by way of example and shall not be construed to be of a limiting nature. It further goes without saying that the term 'charge transfer' between the redox partners is synonymous with a redox reaction between the same.

This applies also to the exemplary embodiments below in which, as in the exemplary embodiments above, a monolayer of hexanedecanethiol was disposed on the collector electrode.

All processing steps are identical to the exemplary embodiments above.

TABLE 2

Further exemplary embodiments for various combinations of substrate, charge transfer mediators and redox species.

| | Collector electrode | Control electrode | Charge transfer mediator | Redox species | Substrate |
|---|---|---|---|---|---|
| 1 | Conductive polymer (PEDOT, PEDOT/PSS, polyaniline) | Conductive polymer (PEDOT, PEDOT/PSS, polyaniline) | Anthracene $E_0 = -1.92$ V | CE(IV) + e±/ Ce(III), $E_0 = 1.3$ V | AlOx |
| 2 | Doped diamond | Doped diamond | Tetramethyl-p-phenylene diamine $E_0 = 0.3$ V | Sn(IV) + 2e*/ Sn(II), $E_0 = -0.1$ V | Glass |

TABLE 2-continued

Further exemplary embodiments for various combinations of substrate, charge transfer mediators and redox species.

| | Collector electrode | Control electrode | Charge transfer mediator | Redox species | Substrate |
|---|---|---|---|---|---|
| 3 | Carbon sp2 hybridized (graphite, carbon nanotubes, graphene) | Carbon sp2 hybridized (graphite, carbon nanolubes, graphene) | Tetrathiafulvalene $-1/-2$ $E_0 = 0.66$ V $0/-1$ $E_0 = 0.3$ V | $Ru(NH3)_6^{3+}$ $Ru(NH3)_6^{2+}$ $E_0 = -0.14$ V | Plastic materials (Plexiglas, PP, PE, PS, silicones, polyolefins) |
| 4 | Elemental semiconductors (silicon, Ge) | Elemental semiconductors (silicon, GE) | Thianthrene $+1/+2$ $E_0 = 1.7$ V $0/+1$ $E_0 = 1.23$ V | Ferrocene II/ Ferrocene III $E_0 = 0.31$ V | Undoped diamond |
| 5 | Compound semiconductors (GaAs, GaP, InP) | Compound semiconductors (GaAs, GaP, InP) | Tetracyanoquinodimethane $-1/-2$ $E_0 = -0.29$ V $0/-1$ $E_0 = 0.13$ V | $Ru(bpy)_3^{2+}/$ $Ru(bpy)_3^{3+}$ $E_0 = 1.32$ V $Ru(bpy)_3^{2+}/$ $Ru(bpy)_3^{1+}$ $E_0 = -1.3$ V | |
| 6 | ITO | ITO | viologen dication $V2+/$ radical cation $V+^*$ $E_0 = -0.42$ V | Dopamine $E_0 = 0.07$ V | |
| 7 | Metals (Ag, Pt, Cu, Pd) | Metals (Ag, Pt, Cu, Pd) | Benzoquinone $-1/-2$ $E_0 = -1.4$ V $0/-1$ $E_0 = -0.54$ V | Benzoquinone $-1/-2$ $E_0 = -1.4$ V $0/-1$ $E_0 = -0.54$ V | |
| 8 | | | Pyrroloquinoline quinone modified glucose oxidase $E_0 = 0.1$ V | Glucose $E_0 = 0.1$ V | |

Lines 1 to 7 of Table 1 are embodiments which, with respect to the circuiting, follow the two previously described exemplary embodiments of circuiting.

Line 8 of the table shows an exemplary embodiment in which a sensor function is described by way of a key-lock reaction for the detection of glucose using glucose oxidase. Here, FAD is initially disposed on the surface of the insulator hexanedecanethiol using an EDC/NHS coupling reaction and then the apoenzyme is provided by immobilization of the glucose oxidase. The reactions for doing so are known from the publication of Zayats et al. (Zayats, M., Katz, E. and Willner, I. (2002). Electrical Contacting of Flavoenzymes and NAD(P)+-Dependent Enzymes by Reconstitution and Affinity Interactions on Phenylboronic Acid Monolayers Associated with Au-Electrodes. J. AM. CHEM. SOC. 124, 14724-14735), which are hereby incorporated by reference in the present patent application. The specific detection of glucose is possible by modulating the voltage to the control electrode.

The invention claimed is:

1. An electrode array for cyclic reduction and oxidation of a redox species in an electrolyte, comprising a control electrode and a collector electrode, wherein both the control and the collector electrodes are disposed on an insulating substrate and connected to a counter electrode for application of a voltage and further comprising a separate reference electrode configured to measure potentials at least at the control electrode and the collector electrode, wherein,
  a) the control electrode is configured for reacting the redox species for cyclic electron transport between the control and the collector electrodes; and
  b) the collector electrode is disposed opposite the control electrode,
  wherein a layer structure composed of a second insulator, having a charge transfer mediator disposed thereon, is additionally disposed on a side of the collector electrode located opposite the insulating substrate for reacting the redox species,
  wherein the control electrode does not have the second insulator and the charge transfer mediator disposed thereon, and
  further wherein the charge transfer mediator and the redox species are both preselected such that the preselected charge transfer mediator and the preselected redox species have a respective standard electrode potential that allows a charge transfer along an electrochemical series as a function of the voltage that is applied by the counter electrode to the control electrode, and by the counter electrode to the collector electrode.

2. The electrode array according to claim 1, wherein the control and the collector electrodes are made of the same material.

3. A method comprising:
  providing an electrode array, for cyclic reduction and oxidation of a redox species in an electrolyte, comprising a control electrode and a collector electrode, wherein both the control and the collector electrodes are disposed on an insulating substrate and connected to a counter electrode for application of a voltage, wherein,
  a) the control electrode is configured for reacting the redox species for cyclic electron transport between the control and the collector electrodes; and
  b) the collector electrode is disposed opposite the control electrode,
  wherein a layer structure composed of a second insulator, having a charge transfer mediator disposed thereon, is additionally disposed on a side of the collector electrode located opposite the insulating substrate for reacting the redox species, and wherein the control electrode does not have the second insulator and the charge transfer mediator disposed thereon;

selecting the charge transfer mediator and the redox species such that the selected charge transfer mediator and the redox species have a respective standard electrode potential that allows a charge transfer along an electrochemical series as a function of the voltage that is applied by the counter electrode to the control electrode, and by the counter electrode to the collector electrode;

selecting the redox species such that the redox species has a more negative standard electrode potential than the standard electrode potential of the charge transfer mediator, the redox species being added to the electrolyte in oxidized form, with a potential that is more negative than the standard electrode potential, of the redox species being applied to the control electrode, and a potential that is more positive than the standard electrode potential of the charge transfer mediator being applied to the collector electrode; and cyclically reacting the redox species at the control electrode and the collector electrode.

4. The electrode array according to claim 1, wherein the control electrode and the collector electrode have a constant distance of less than 10 µm.

5. The electrode array according to claim 1, wherein the control and the collector electrodes are arranged in the same plane on the substrate insulator, or on top of each other.

6. The electrode array according to claim 1, wherein the charge transfer mediator comprises 11-undecanethio ferroncene (Fc) and the second insulator comprises hexanedecanethio (HDT).

7. The electrode array according to claim 2, wherein the same material of the control electrode and the collector electrode is gold and the control electrode does not have any further molecule layers thereon.

8. A method comprising:
providing an electrode array, for cyclic reduction and oxidation of a redox species in an electrolyte, comprising a control electrode and a collector electrode,
wherein both the control and the collector electrodes are disposed on an insulating substrate and connected to a counter electrode for application of a voltage, wherein,
a) the control electrode is configured for reacting the redox species for cyclic electron transport between the control and the collector electrodes; and
b) the collector electrode is disposed opposite the control electrode,
wherein a layer structure composed of a second insulator, having a charge transfer mediator disposed thereon, is additionally disposed on a side of the collector electrode located opposite the insulating substrate for reacting the redox species, and
wherein the control electrode does not have the second insulator and the charge transfer mediator disposed thereon;
selecting the charge transfer mediator and the redox species such that the selected charge transfer mediator and the redox species have a respective standard electrode potential that allows a charge transfer along an electrochemical series as a function of the voltage that is applied by the counter electrode to the control electrode, and by the counter electrode to the collector electrode;
selecting the redox species such that the redox species has a more positive standard electrode potential than the standard electrode potential of the charge transfer mediator, the redox species being added to the electrolyte in reduced form, with a potential that is more positive than the standard electrode potential of the redox species being applied to the control electrode, and a potential that is more negative than the standard electrode potential of the charge transfer mediator being applied to the collector electrode; and
cyclically reacting the redox species at the control electrode and the collector electrode.

9. A method comprising:
providing an electrode array, for cyclic reduction and oxidation of a redox species in an electrolyte, comprising a control electrode and a collector electrode,
wherein both the control and the collector electrodes are disposed on an insulating substrate and connected to a counter electrode for application of a voltage, wherein,
a) the control electrode is configured for reacting the redox species for cyclic electron transport between the control and the collector electrodes; and
b) the collector electrode is disposed opposite the control electrode,
wherein a layer structure composed of a second insulator, having a charge transfer mediator disposed thereon, is additionally disposed on a side of the collector electrode located opposite the insulating substrate for reacting the redox species, and
wherein the control electrode does not have the second insulator and the charge transfer mediator disposed thereon;
selecting the charge transfer mediator and the redox species such that the selected charge transfer mediator and the redox species have a respective standard electrode potential that allows a charge transfer along an electrochemical series as a function of the voltage that is applied by the counter electrode to the control electrode, and by the counter electrode to the collector electrode; and
cyclically reacting the redox species at the control electrode and the collector electrode and selecting an upper and a lower limit current at the collector electrode which, when said upper and lower limit currents are exceeded or no longer met, the charge transfer is established at the collector electrode or control electrode as a positive or negative event.

10. A method comprising:
providing an electrode array, for cyclic reduction and oxidation of a redox species in an electrolyte, comprising a control electrode and a collector electrode,
wherein both the control and the collector electrodes are disposed on an insulating substrate and connected to a counter electrode for application of a voltage, wherein,
a) the control electrode is configured for reacting the redox species for cyclic electron transport between the control and the collector electrodes; and
b) the collector electrode is disposed opposite the control electrode,
wherein a layer structure composed of a second insulator, having a charge transfer mediator disposed thereon, is additionally disposed on a side of the collector electrode located opposite the insulating substrate for reacting the redox species, and
wherein the control electrode does not have the second insulator and the charge transfer mediator disposed thereon;

selecting the charge transfer mediator and the redox species such that the selected charge transfer mediator and the redox species have a respective standard electrode potential that allows a charge transfer along an electrochemical series as a function of the voltage that is applied by the counter electrode to the control electrode, and by the counter electrode to the collector electrode; and cyclically reacting the redox species at the control electrode and the collector electrode and creating a transistor-like current amplification at the collector electrode by modulation of the voltage at the control electrode.

\* \* \* \* \*